US012599618B2

(12) United States Patent
Braile et al.

(10) Patent No.: US 12,599,618 B2
(45) Date of Patent: *\*Apr. 14, 2026**

(54) SYSTEM AND METHOD FOR AEROBIC RESPIRATORY TREATMENT

(71) Applicants: Jeff Braile, Boca Raton, FL (US);
Morgan Pepitone, Boca Raton, FL (US)

(72) Inventors: Jeff Braile, Boca Raton, FL (US);
Morgan Pepitone, Boca Raton, FL (US)

( * ) Notice: Subject to any disclaimer, the term of this patent is extended or adjusted under 35 U.S.C. 154(b) by 379 days.

This patent is subject to a terminal disclaimer.

(21) Appl. No.: 18/378,020

(22) Filed: Oct. 9, 2023

(65) Prior Publication Data

US 2024/0033275 A1      Feb. 1, 2024

Related U.S. Application Data

(63) Continuation-in-part of application No. 17/554,057, filed on Dec. 17, 2021, now Pat. No. 11,779,621.

(51) Int. Cl.
A61K 31/00          (2006.01)
A61K 9/50          (2006.01)

(52) U.S. Cl.
CPC .............. *A61K 31/658* (2023.05); *A61K 9/50* (2013.01)

(58) Field of Classification Search
None
See application file for complete search history.

(56) References Cited

U.S. PATENT DOCUMENTS 9,655,936 B2 *   5/2017   Ruben ................. A61K 36/185

* cited by examiner

*Primary Examiner* — Michael V Meller
(74) *Attorney, Agent, or Firm* — Malloy & Malloy, P.L.; Robert M. Downey

(57) ABSTRACT

A method of producing pure cannabidiol (CBD) isolate crystals including the steps of extracting the CBD compound from a cannabis plant; winterizing to remove fats, waxes and chlorophyll from the CBD extract; filtering the CBD extract through a series of filter plates; removing carboxylic acid and CO2 from the CBD extract; removing impurities from the CBD extract by distillation; and crystallizing the purified CBD extract to produce pure CBD isolate crystals and chopping the pure CBD isolate crystals to produce crystals of between 200 and 600 microns in size. A further embodiment includes the steps of grinding the CBD isolate crystals and salt to produce micro-particles of between 1 and 40 microns and/or macro-particles of between 41 and 100 microns and releasing the particles into an air environment.

3 Claims, 3 Drawing Sheets

SYSTEM AND METHOD FOR AEROBIC RESPIRATORY TREATMENT

This non-provisional patent application is a Continuation-In-Part (CIP) of co-pending non-provisional patent application Ser. No. 17/554,057 filed on Dec. 17, 2021.

BACKGROUND OF THE INVENTION

Field of the Invention

The present invention relates to cannabidiol (CBD) isolate, and more particularly, to a method of extracting, purifying and crystallizing CBD isolate for use in aerobic respiratory treatment.

Description of the Related Art

Cannabidiol (CBD) is one of many cannabinoids found in cannabis plants and accounts for up to 40% of the plant's extract. Cannabidiol is a versatile compound and can be used in various ways to promote overall health and wellness. Currently, CBD is used in a variety of ways, including in food and beverage products, oral delivery over-the-counter pills and capsules, oils and tinctures, and topicals that can be applied to the skin, hair and nails.

According to recent research, the global cannabidiol (CBD) market size was valued at USD $2.8 billion in 2020 and is expected to expand at a compound annual growth rate (CAGR) of 21.2% from the year 2021 to the year 2028. Due to its believed healing properties, the demand for CBD for health and wellness purposes is high, which is the major factor driving the market growth. In addition, the rising acceptance and use of products containing CBD, as a result of government approvals and expected future approvals, is a major factor that will most likely boost production of CBD-infused products.

The recent COVID pandemic has focused increased attention on the need for improved healthy lung function. Recent studies have implied that CBD in tincture form has been effective in increasing healthier lung function in COVID patients. In particular, a 2020 study from the Dental College of Georgia and the Medical College of Georgia, both in Augusta, Georgia, have produced results showing that CBD reduces damage in the lungs spurred by cytokine storms caused by Coronavirus (COVID-19). In an earlier study, researchers illustrated that CBD can reduce inflammation and physical lung damage associated with Adult Respiratory Distress Syndrome (ARDS), along with improved oxygen levels. A more recent study revealed the mechanisms behind these earlier results, exhibiting that CBD normalizes levels of apelin, a peptide known to reduce inflammation. During a COVID-19 infection, levels of the apelin peptide are low. Results of this study have been published in the Journal of Cellular and Molecular Medicine. Additionally, a 2015 study on Guinea pigs showed CBD helped open up the bronchial passages. Researchers believe it's possible that CBD could help people with Chronic Obstructive Pulmonary Disease (COPD) breathe easier and keep blood oxygen levels from falling too low. Finally, a 2014 study on mice with damaged lungs showed that CBD helped lower inflammation and improved lung function.

Other cannabinoids (e.g., CBG, CBN) also have known health benefits and are fully contemplated for use within the system and method of the present invention. Moreover, synthetic forms of cannabinoids that may be developed in the future are fully contemplated within the scope of the present invention.

CBD isolate crystals that are miniaturized into microscopic particles and released into the environment to be inhaled into the lungs and sinuses is the purest way of ingesting CBD into the body.

Pharmaceutical salt when inhaled in microscopic particles has been used for decades as an anti-inflammatory for the respiratory channels. CBD has also been noted to have anti-inflammatory properties. In addition, CBD provides benefit to individuals suffering from anxiety. It is postulated that CBD helps to increase serotonin uptake in the brain. Since serotonin is a modulator of the respiratory network this could be acting to differentially effect frequency and amplitude of respiratory activity. Additional benefits of CBD include enhanced energy and focus. These also are related to the effect on the brain. In terms of CBD for focus, CBD's main targets are CB1 and CB2 receptors that specialize in regulating neurotransmitter function, reducing anxiety, and promoting calmness. By interacting with those receptors and causing some alterations, CBD may allow a person to achieve enhanced mental clarity.

The resultant CBD isolate or other cannabinoid isolate produced by the method of the invention has a delta-9 tetrahydrocannabinol [THC] concentration of not more than 0.3 percent on a dry weight basis or such other limit permitted under US federal law. And in at least one embodiment of the invention, the resultant CBD isolate or other cannabinoid isolate has a zero concentration of THC (i.e., THC free).

SUMMARY OF THE INVENTION

The present invention is directed to a method of extracting, purifying and crystallizing cannabidiol (CBD) isolate and a system for delivering pure CBD isolate crystals into an air environment for inhalation into the lungs and sinuses for purposes of respiratory health. In several embodiments of the invention, micro crystallized CBD is combined with micro crystallized salt according to various percentages of each component of the mixture and the mixture of micro crystallized CBD and salt is released into the air environment for inhalation into the lungs, sinuses and respiratory channels for purposes of respiratory health and enhanced mental clarity.

According to the present invention, the method of extracting, purifying and crystallizing CBD isolate includes the steps of: extraction; winterization; filtration; decarboxylation; distillation; and crystallization. The step of extraction uses either hydrocarbon solvent or ethanol solvent to extract the CBD compound from the cannabis plant. The step of winterization removes fats, waxes and chlorophyll from the CBD extract to increase purity of the CBD compound. In filtration, a filter press is used with the assistance of a vacuum pump to pull the mixture through a series of filter plates. Fats, waxes and other impurities are collected in one vessel and the desired miscella is collected in another vessel. In the step of decarboxylation, carboxylic acid and $CO_2$ are removed from the cannabinoid in the extract. Next, in distillation, the extract is loaded into a feed tank, under vacuum, where it passes over a heated rotating plate. From there, the heated extract then enters a secondary vessel where spinning wipers create a thin film around the heated, jacketed vessel as vapors separate. The vapors are then condensed back into liquid form. Receiving vessels then collect the main body CBD that has been separated from the terpenes, volatiles and high boiling point cannabinoids. Finally, in the crystallization step, the CBD liquid mixture is directed into a large vat, or reactionary vessel, with a stirring attachment. The mixture is heated and then cooled to cause the CBD oil to crystallize and separate from the solution. After this, the crystals are rinsed with a chemical solvent, to remove any remaining unwanted impurities and are processed through a chopping device to produce crystals of between 200 and 600 microns in size.

According to the aerobic respiratory treatment system of the present invention, the CBD isolate crystals are then miniaturized by either a specifically formatted generator or a handheld device to produce micro-particles of between 1 and 100 microns in size, including microscopic particles ranging between 1-40 microns and macroscopic particles ranging between 41-100 microns, that are released into an air environment to allow the crystallized particles to be inhaled into the lungs and sinuses. The miniaturization of the CBD isolate crystals may be achieved by a blade mechanism and a fan contained either in a generator or handheld device, or a tabletop unit, to produce the particles which are released and suspended in the air where they can be inhaled directly into the nose and mouth.

In a further embodiment of the present invention, the crystallized particles of CBD isolate may be combined with particles of pharmaceutical grade salt which together are released into the air environment to be inhaled into the lungs and sinuses. Once inhaled, these crystallized CBD isolate particles and salt particles absorb irritants, including allergens and toxins, from the respiratory system. This helps to break up mucus and reduces inflammation, resulting in clear airways.

When salt is combined with CBD, in particle form for inhalation into the lungs, a multiplier effect is created due to the benefits of the CBD. More particularly, the compound created by the mixture of micro crystallized CBD and salt provides multiple benefits for both respiratory health as well as mental wellbeing. The combination of salt and crystallized CBD may be miniaturized into particles by a generator apparatus or handheld generator device and released into the air environment for direct inhalation through the nose and/or mouth and into the respiratory channels and lungs.

In a further embodiment of the invention, the CBD and salt combination may be miniaturized into particles and then aerosolized through a handheld nebulizer or canister designed to propel the particles toward the nose and mouth where it can enter the nasal cavity, respiratory channels and lungs.

BRIEF DESCRIPTION OF THE DRAWINGS

For a fuller understanding of the nature of the present invention, reference should be had to the following detailed description taken in connection with the accompanying drawing in which.

Like reference numerals refer to like parts throughout the several views of the drawings.

DETAILED DESCRIPTION OF THE PREFERRED EMBODIMENT

Figure 1:
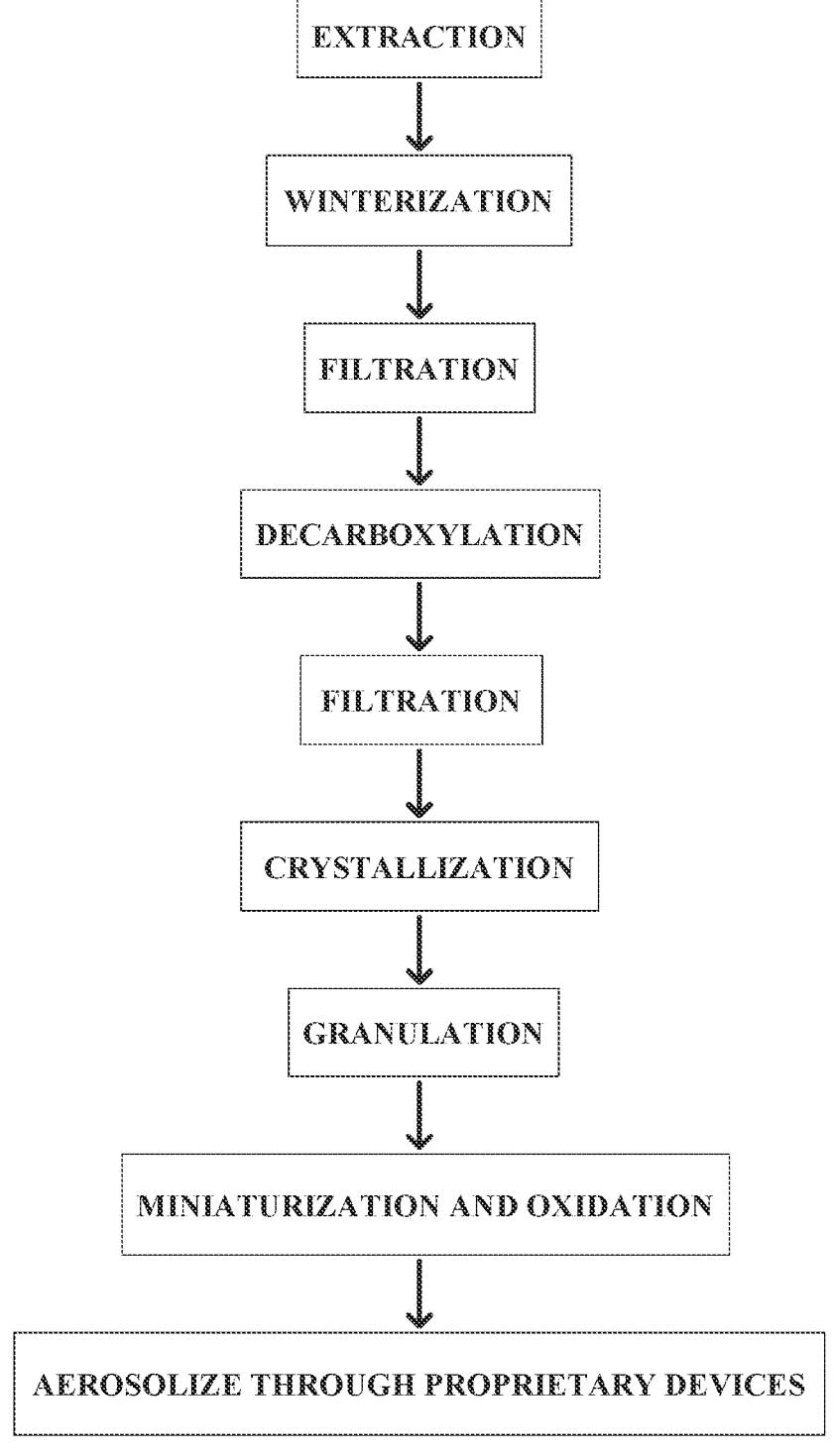
FIG. 1 is a flow chart, in schematic form, illustrating the sequence of steps in the process of producing pure crystallized CBD isolate according to the method of the present invention.

The present invention provides a method of producing pure CBD isolate, in crystallized form and a method of delivering crystallized CBD particles into an air environment to be inhaled deep into the lungs and sinuses for therapeutic benefits of CBD on the lungs and sinuses to thereby increase respiratory health and function. The present invention further contemplates the use of all cannabinoids, such as, for example, CBG and CBN, in the system and method of the present invention which delivers pure crystallized cannabinoid isolate particles in a suspended form in the air environment for inhalation into the lungs and sinuses, thereby providing the desired therapeutic benefits to increase respiratory health and function.

The process of producing pure CBD isolate in crystallized form includes the steps of: extraction; winterization; filtration; decarboxylation; distillation; and crystallization. In the step of extraction, hydrocarbon solvent, like butane or propane, or ethanol solvent is used to extract the cannabidiol (CBD) extract from the cannabis plant. In the step of winterization, fats, waxes and chlorophyll are removed from the CBD extract. This helps to increase the purity of the CBD extract with the highest percentage of CBD in the resultant isolate. In winterization, the CBD extracted from the cannabis plant is cooled down to sub-zero temperatures in combination with a solvent. Then, maintaining that chilled environment for a period of time to allow the lipids (fats and waxes) to coagulate and separate from the oils in the extract. Next, in filtration, a filter press is used with the assistance of a vacuum pump to pull the CBD extract/solvent mixture through a series of filter plates. In this process, more fats, waxes and other impurities are collected in one vessel and the desired miscella is collected in another vessel.

The step of decarboxylation removes carboxylic acid and $CO_2$ from cannabinoids present in the CBD extract. Converting the acidic cannabinoid (CBDa) to its neutral form (CBD) ensures the end product contains all of the several benefits that cannabidiol has to offer. The decarboxylation process is achieved through the application of heat in a reactionary vessel. In the step of distillation, the extract is loaded into a feed tank, under vacuum, where it passes over a heated rotating plate. From there, the heated oil then enters a secondary vessel where there are spinning wipers that are used to create a thin film of the extract around the heated, jacketed vessel. A long condensing coil in the middle of the vessel, cooled with circulating fluid, recondenses the vapors back into liquid form. Receiving vessels then collect the main body CBD from the terpenes, volatiles and high boiling point cannabinoids. Finally, the crystallization step is started by putting the CBD oil extract into a large vat, or reactionary vessel, with a stirring attachment. The mixture is heated, while constantly being stirred throughout the heating process. Then, after heating, the temperature is lowered and the rate of stirring is slowed down. Once the mixture has cooled and nucleation starts to occur (i.e., the initial stages of crystallization), the stirring rate is drastically increased, which causes the crystals to separate from the solution. After this, the crystals are rinsed with pentane, or other chemical solvent to remove any remaining unwanted impurities.

The resultant CBD isolate or other cannabinoid isolate produced by the method of the invention has a delta-9 tetrahydrocannabinol [THC] concentration of not more than 0.3 percent on a dry weight basis or such other limit permitted under US federal law. And in at least one embodiment of the invention, the resultant CBD isolate or other cannabinoid isolate has a zero concentration of THC (i.e., THC free).

In a next step of granulation, the CBD isolate crystals or other comparable substance is then further refined into small crystals between 200 and 600 microns in size. In a next step of miniaturization and oxidation, the crystallized isolate is directed through proprietary devices or generators consisting of a blade mechanism which is programmed to accurately grind and/or cut the isolate crystals into precise particles having a size of between 1 and 100 microns. These particles are then propelled into the air or an enclosed environment where they combine with oxygen and can be inhaled into the nose and mouth. Other microscopic particles (1-40 microns in size) will fall on the skin where health benefits can also be achieved.

The crystallized CBD isolate micro-particles are released by a fan-driven device or a blower apparatus that release the CBD isolate crystallized particles into the air atmosphere for direct inhalation into the lungs and sinuses. Prior to miniaturization, the crystallized CBD isolate particles may be combined with microscopic salt particles for release into the air environment. When the fine microscopic particles are inhaled, they fall on the airway linings and draw water into the airway, thinning the mucus and making it easier to raise, thus making people feel better. This process also reduces inflammation and results in clearer airways.

It is also proposed that the crystallized CBD isolate crystallized micro-particles, alone or in combination with microscopic size pharmaceutical grade salt particles, have a similar effect on the skin by absorbing bacteria and other impurities responsible for many skin conditions. This process thus allows for health benefits to the skin as microscopic particles will fall on the face and body when respiratory therapy using the system and method of the present invention is performed in an enclosed environment. The anti-inflammatory particles of CBD may be particularly useful for reducing potential triggers of eczema, dermatitis, and psoriasis. Just as CBD oil is known to help soothe skin and reduce the appearance of irritation, the combined CBD isolate crystallized micro-particles and pharmaceutical grade salt microscopic particles may be useful for people with sensitive skin. This therapeutic treatment may also be found to be beneficial for the treatment of acne and other skin conditions.

As previously noted, the inhalation of pharmaceutical grade salt particles has been used for decades as an anti-inflammatory for the respiratory channels. The present invention proposes to combine pharmaceutical grade salt particles with the pure CBD isolate crystallized particles to be released into the air for inhalation into the lungs, sinuses and respiratory channels for purposes of respiratory health and enhanced mental clarity. According to the method of the present invention, in the composition of CBD isolate crystals and salt, the CBD isolate crystallized particles are present in an amount of between 0.5% and 55% by weight of the composition and the particles of pharmaceutical grade salt are present in an amount of between 45% and 99.5% by weight of the composition. The following are examples of compositions comprising the combination of the crystallized particles of CBD isolate and particles of pharmaceutical grade salt for use in respiratory treatment, wherein the composition of CBD isolate crystal particles and pharmaceutical grade salt particles are released into the air environment for inhalation into the lungs, sinuses and respiratory channels.

---

EXAMPLE 1

| | |
|---|---|
| CBD isolate crystallized particles: | 0.5% by weight of the composition |
| Pharmaceutical grade salt particles: | 99.5% by weight of the composition |

---

EXAMPLE 2

| | |
|---|---|
| CBD isolate crystallized particles: | 2.5% by weight of the composition |
| Pharmaceutical grade salt particles: | 97.5% by weight of the composition |

---

EXAMPLE 3

| | |
|---|---|
| CBD isolate crystallized particles: | 5% by weight of the composition |
| Pharmaceutical grade salt particles: | 95% by weight of the composition |

---

EXAMPLE 4

| | |
|---|---|
| CBD isolate crystallized particles: | 10% by weight of the composition |
| Pharmaceutical grade salt particles: | 90% by weight of the composition |

---

EXAMPLE 5

| | |
|---|---|
| CBD isolate crystallized particles: | 20% by weight of the composition |
| Pharmaceutical grade salt particles: | 80% by weight of the composition |

---

EXAMPLE 6

| | |
|---|---|
| CBD isolate crystallized particles: | 30% by weight of the composition |
| Pharmaceutical grade salt particles: | 70% by weight of the composition |

---

EXAMPLE 7

| | |
|---|---|
| CBD isolate crystallized particles: | 40% by weight of the composition |
| Pharmaceutical grade salt particles: | 60% by weight of the composition |

---

EXAMPLE 8

| | |
|---|---|
| CBD isolate crystallized particles: | 50% by weight of the composition |
| Pharmaceutical grade salt particles: | 50% by weight of the composition |

---

EXAMPLE 9

| | |
|---|---|
| CBD isolate crystallized particles: | 55% by weight of the composition |
| Pharmaceutical grade salt particles: | 45% by weight of the composition |

Figure 2:
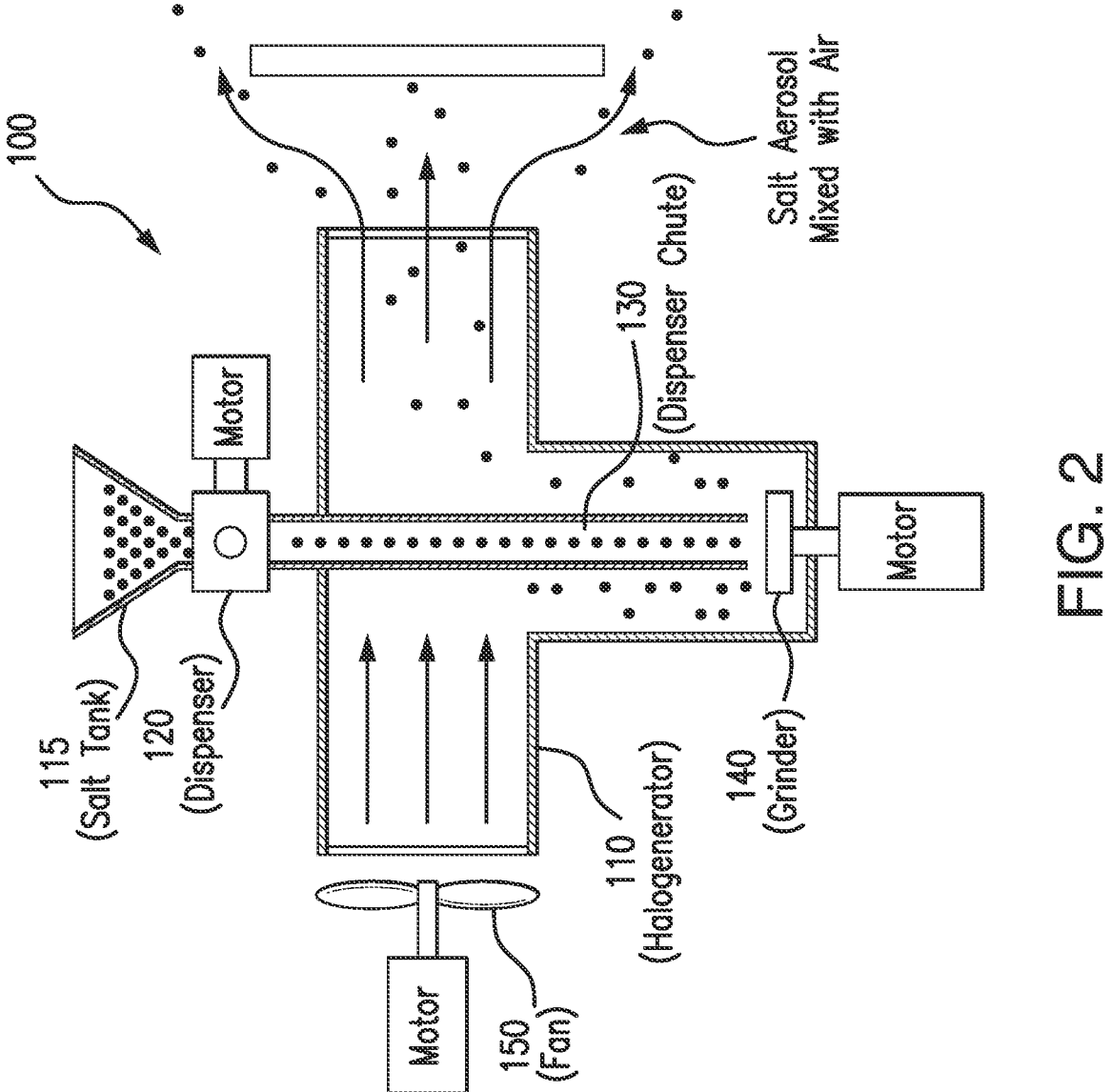
FIG. 2 is a general diagram showing the main components of a generator device in accordance with one embodiment for miniaturizing the CBD isolate crystals in combination with pharmaceutical grade salt and releasing the particles into the surrounding air atmosphere where they can be inhaled directly into the nose and mouth.

Referring to FIG. 2, a general diagram of a generator apparatus is shown for miniaturizing the CBD isolate crystals into precise particles having a size of between 1 and 100 microns, including microscopic particles ranging between 1 and 40 microns in size and macroscopic particles ranging between 41 and 100 microns in size. As noted above, pharmaceutical grade salt may also be combined with the CBD isolate crystals and also miniaturized to the precise size of between 1 and 100 microns. The generator apparatus is particularly in the form of a halo generator 110 that includes a hopper or salt tank 115 within which is fed the CBD isolate crystals alone or in combination with the pharmaceutical grade salt. A motorized dispenser 120 releases the CBD isolate crystals as well as the pharmaceutical grade salt crystals, if desired, through a dispenser shoot 130 where the crystals are then further grinded by a motorized grinder 140 having a blade mechanism that accurately grinds and/or cuts the CBD isolate crystals, as well as the pharmaceutical grade salt, into the desired particle size of between 1 and 100 microns. A motorized fan 150 blows the particles out from the opposite side of the halo generator, to release the CBD isolate crystallized particles, as well as the pharmaceutical grade salt particles into the air atmosphere for direct inhalation into the lungs and sinuses. It should be noted that the halo generator 110 can be used to grind and release only the CBD isolate crystallized particles in the event it is not desired to combine the pharmaceutical grade salt with the CBD isolate crystals. It is also noted that other cannabinoid isolates, such as, for example, CBG and/or CBN, may be used in the generator apparatus 100 to deliver the pure crystallized cannabinoid isolate particles in a suspended form in the air environment for inhalation into the lungs and sinuses, to thereby provide the desired therapeutic benefits. The other contemplated cannabinoid isolate crystals are produced in the same or similar series of steps as set forth above.

Figure 3:
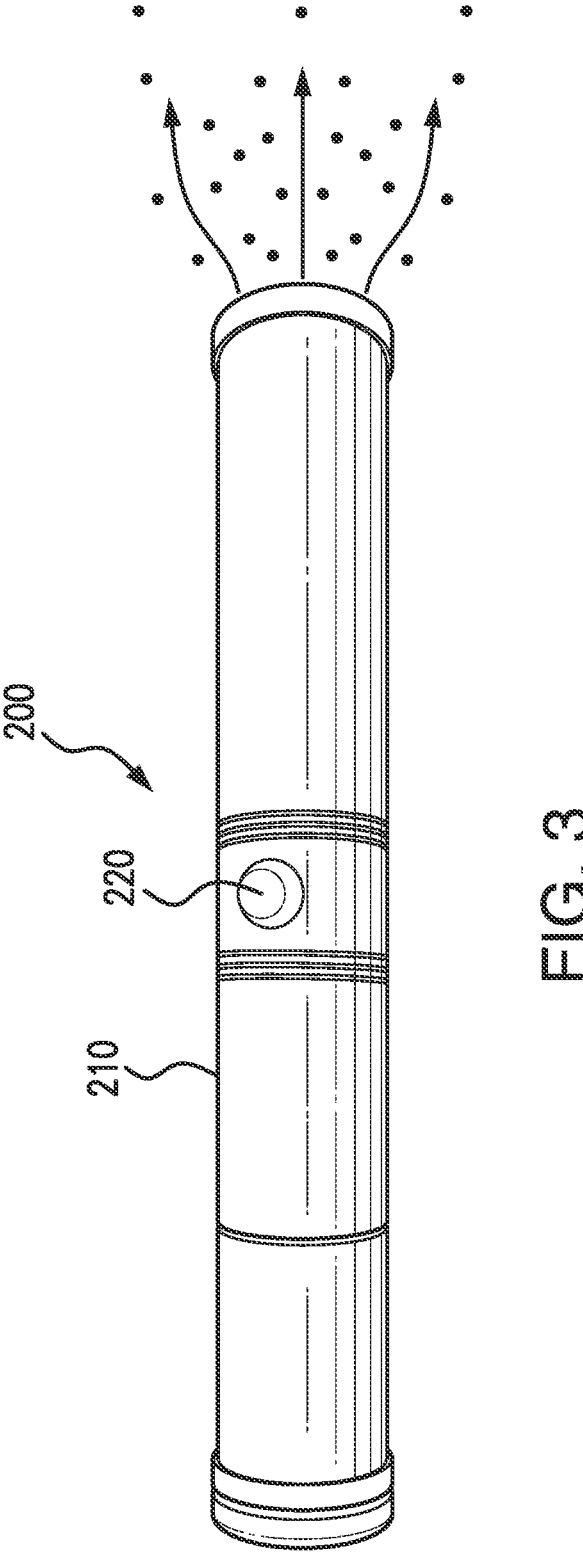
FIG. 3 is a perspective view of a handheld generator device for miniaturizing the CBD isolate crystals, which can be combined with a pharmaceutical grade salt, and releasing the particles for direct inhalation by the user through the nose and/or mouth, in accordance with another embodiment of the invention.

FIG. 3 illustrates a handheld generator device 200 that is used to grind and release the cannabinoid micro-particles for inhalation through the nose and/or mouth of a user. Similar to the generator apparatus of FIG. 2, the cannabinoid crystal isolate, such as crystallized CBD isolate may be combined with pharmaceutical grade salt and ground within the handheld device 200 for releasing the particles in a size of between 1 and 100 microns, for inhalation by the user. The handheld device 200 is preferably in the form of an elongate tube 210 that contains the motorized blower, grinder and chamber for holding the cannabinoid isolate crystals and/or pharmaceutical grade salt crystals. Operation of a button 220 or other actuator mechanism serves to acuate the grinder and the blower within the handheld device 200 to release the particles, as shown in FIG. 3.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method of producing pure cannabidiol isolate crystals comprising the steps of:
   a) extracting cannabidiol from cannabis to produce a cannabidiol extract;
   b) removing fats, waxes and chlorophyll from the cannabidiol extract to increase purity of the cannabidiol;
   c) filtering the cannabidiol extract to produce filtered cannabidiol extract;
   d) heating the cannabidiol extract to produce vapors and remove impurities;
   e) condensing the vapors from the heated cannabidiol extract into purified liquid form;
   f) collecting the purified liquid form cannabidiol;
   g) heating the purified liquid form cannabidiol;
   h) cooling the purified liquid form cannabidiol to produce a purified cannabidiol oil mixture;
   i) crystallizing the purified cannabidiol oil mixture under cooling to yield pure cannabidiol isolate crystals;
   j) rinsing the pure cannabidiol isolate crystals with a solution to remove remaining unwanted impurities;
   k) directing the pure cannabidiol isolate crystals through a chopping or cutting device to produce pure cannabidiol isolate crystals of between 200 microns and 1,200 microns in size;
   l) miniaturizing the pure cannabidiol isolate crystals to produce particles of pure cannabidiol isolate crystals of between 1 and 100 microns in size;
   m) producing particles of pharmaceutical grade salt of between 1 and 100 microns in size; and
   n) combining the particles of pure cannabidiol isolate crystals with the particles of pharmaceutical grade salt and releasing the combined mixture into the environment.

2. The method of claim 1, wherein the particles of pure cannabidiol isolate crystals are present in an amount of between 0.5% and 55% by weight of the combined mixture of pharmaceutical grade salt and pure cannabidiol isolate crystals.

3. The method of claim 1, wherein the particles of pharmaceutical grade salt are present in an amount of between 45% and 99.5% by weight of the combined mixture of pure cannabidiol isolate crystals and pharmaceutical grade salt.

* * * * *